United States Patent
Subra et al.

(10) Patent No.: US 11,987,708 B2
(45) Date of Patent: *May 21, 2024

(54) **PROCESS FOR PREPARING A *LAWSONIA INERMIS* EXTRACT**

(71) Applicant: PIERRE FABRE DERMO-COSMETIQUE, Boulogne-Billancourt (FR)

(72) Inventors: Laurent Subra, Montgaillard (FR); Jean-Marie Autret, Gaillac (FR); Christel Fiorini-Puybaret, Toulouse (FR); Philippe Joulia, Villenouvelle (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 163 days.

This patent is subject to a terminal disclaimer.

(21) Appl. No.: 17/608,325

(22) PCT Filed: Jun. 12, 2020

(86) PCT No.: PCT/EP2020/066329
§ 371 (c)(1),
(2) Date: Nov. 2, 2021

(87) PCT Pub. No.: WO2020/249746
PCT Pub. Date: Dec. 17, 2020

(65) Prior Publication Data
US 2022/0204776 A1    Jun. 30, 2022

(30) Foreign Application Priority Data
Jun. 12, 2019   (FR) ........................... 1906264

(51) Int. Cl.
*C09B 61/00* (2006.01)
*A61K 8/35* (2006.01)
(Continued)

(52) U.S. Cl.
CPC .............. *C09B 61/00* (2013.01); *A61K 8/35* (2013.01); *A61K 8/498* (2013.01); *A61K 8/922* (2013.01);
(Continued)

(58) Field of Classification Search
CPC . C09B 61/00; C09B 67/0092; C09B 67/0096; C09B 67/006; A61K 8/35;
(Continued)

(56) References Cited

U.S. PATENT DOCUMENTS

| | | | |
|---|---|---|---|
| 11,684,561 B2 * | 6/2023 | Fiorini-Puybaret | C09B 61/00 8/428 |
| 11,707,428 B2 * | 7/2023 | Fiorini-Puybaret | A61K 8/9789 8/405 |
| 2007/0251024 A1 * | 11/2007 | Greaves | A61Q 5/065 8/405 |

FOREIGN PATENT DOCUMENTS

| | | |
|---|---|---|
| FR | 2 473 310 A1 | 7/1981 |
| WO | WO 99/15145 A1 | 4/1999 |
| WO | WO 00/12108 A1 | 3/2000 |

OTHER PUBLICATIONS

El-Shaer et al., "Determination of lawsone in henna powders by high performance thin layer chromatography," J. Sep. Sci., vol. 30, 2007, pp. 3311-3315.
(Continued)

*Primary Examiner* — Eisa B Elhilo
(74) *Attorney, Agent, or Firm* — Birch, Stewart, Kolasch & Birch, LLP

(57) ABSTRACT

The present disclosure relates to a process for preparing a *Lawsonia inermis* extract which is rich in Lawsone. It also (Continued)

relates to the extract which may be obtained by said process and to a composition comprising thereof. The disclosure also relates to a method for dying fibers, in particular keratin fibers.

16 Claims, 1 Drawing Sheet

(51) Int. Cl.
  *A61K 8/49* (2006.01)
  *A61K 8/92* (2006.01)
  *A61Q 5/06* (2006.01)
  *C07C 46/10* (2006.01)
(52) U.S. Cl.
  CPC .............. *A61Q 5/065* (2013.01); *C07C 46/10* (2013.01); *A61K 2236/33* (2013.01)
(58) Field of Classification Search
  CPC .... A61K 8/498; A61K 8/922; A61K 2236/33; A61K 8/34; A61K 8/355; A61Q 5/065; C07C 46/10
  USPC ............................................................ 8/435
  See application file for complete search history.

(56) References Cited

OTHER PUBLICATIONS

English translation of the International Search Report and Written Opinion of the International Searching Authority for International Application No. PCT/EP2020/066329, dated Aug. 6, 2020.
French Preliminary Search Report and Written Opinion for French Application No. 1906264, dated Feb. 20, 2020.
Gallo et al., "Henna through the centuries: a quick HPTLC anaylsis proposal to check henna identity," Rev Bras Farmacogn, vol. 24, 2014, pp. 133-140.
Hsouna et al., "Antioxidant constituents from Lawsonia inermis leaves: Isolation, structure elucidation and antioxidative capacity," Food Chemistry, vol. 125, 2011, pp. 193-200.
Huh et al., "A cell-based system for screening hair growth-promoting agents," Arch Dermatol Res, vol. 301, 2009 (Published online Mar. 11, 2009), pp. 381-385.
Nichols et al., "Skin photoprotection by natural polyphenols: Anti-inflammatory, anti-oxidant and DNA repair mechanisms," Arch Dermatol Res., vol. 302, No. 2, Mar. 2010, pp. 1-19.
Saewan et al., "Photoprotection of natural flavonoids," Journal of Applied Pharmaceutical Science, vol. 3, No. 9, Sep. 2013, pp. 129-141.
Zohourian et al., "Polyphenolic Contents and Antioxidant Activities of Lawsonia Inermis Leaf Extracts Obtained by Microwave-assisted Hydrothermal Method," Journal of Microwave Power and Electromagnetic Energy, vol. 45, No. 4, 2011, pp. 193-204 (13 pages total).

* cited by examiner

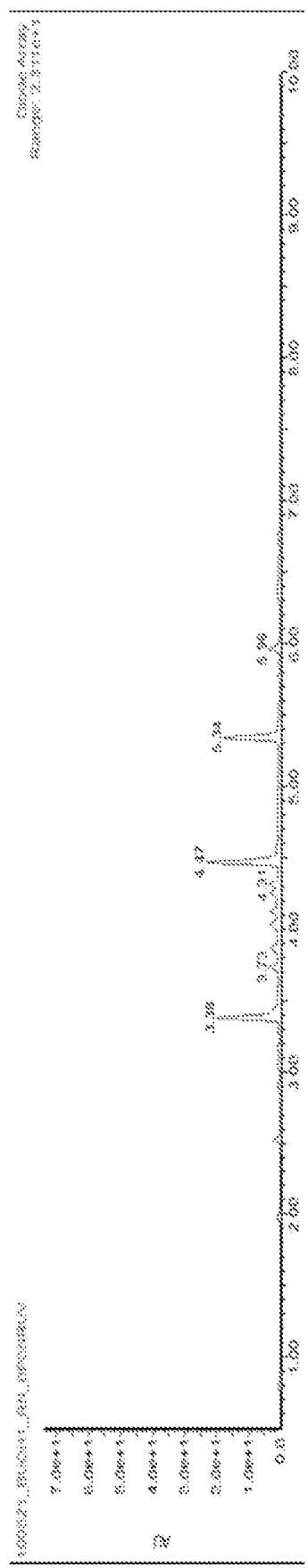

PROCESS FOR PREPARING A *LAWSONIA INERMIS* EXTRACT

TECHNICAL FIELD

The present invention relates to a process for preparing a *Lawsonia inermis* extract which is rich in Lawsone. It also relates to an extract of *Lawsonia inermis* which may be obtained by said process and to compositions comprising thereof. The invention also relates to a method for dying fibers, in particular keratin fibers.

BACKGROUND

*Lawsonia inermis*, commonly called henna, belongs to the Lythraceae family. This shrub, which can reach a height of 6 meters, grows naturally in the tropical and subtropical regions of Africa and Asia, notably. It has a gray bark, dense branching, and quadrangular and thorny branches on the oldest ones. Its leaves grow opposite each other and are simple and whole. The scented white or red flowers are grouped in large pyramidal panicles of 25 cm long.

Henna leaves, which produce red and orange tints, have been used for more than 5000 years for dying hair and skin, or even textile dying.

Their dye properties are due to lawsone (2-hydroxy-1,4-naphthoquinone), which reacts with the keratin present in the skin or nails by a Michael addition.

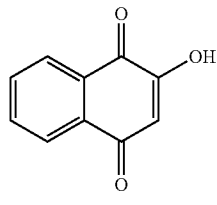
Lawsone

Generally, lawsone is able to undergo this type of condensation with various compounds containing an amino group, such as proteins, peptides or amino acids. This is why the commercially-available henna extracts have a relatively low lawsone content, which also decreases quickly over time.

Moreover, the quantity of lawsone found in the free state in *Lawsonia inermis* leaves is actually very small. In fact, it is predominantly present in the form of heterosides [Gallo et al. *Rev. Bras. Pharmacogn.* 2014, 23, 133-140; COLIPA no. C169, 2013].

Hennosides A, B and C, which are monoglycosylated lawsone derivatives, have notably been identified.

Hydrolysis of these precursors, followed by autooxidation of the resulting aglycone, leads to the formation of lawsone according to the reaction scheme indicated below.

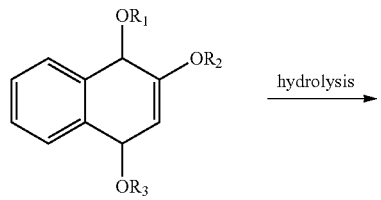

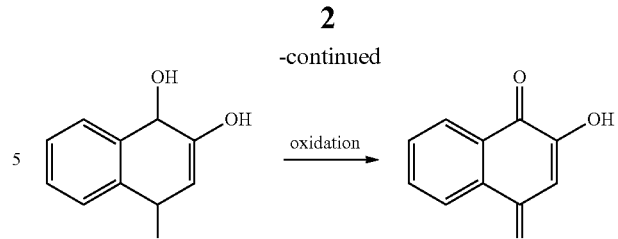

$R_1$=glucose, $R_2$=$R_3$=H;
$R_2$=glucose; $R_1$=$R_3$=H; or
$R_3$=glucose; $R_1$=$R_2$=H.

Thus, a number of known extraction processes for *Lawsonia inermis* include a step in acidic medium, typically at a pH comprised between 1 and 3, during which the hennosides are hydrolyzed.

An extraction process is notably described in document FR2473310.

SUMMARY

The invention relates to a process for preparing a lawsone-rich extract which comprises the steps of:
a) macerating the aerial parts of *Lawsonia inermis* in water, at a pH ranging from 4 to 8 in order for the glycosylated lawsone derivatives, such as hennosides, initially present in the aerial parts of *Lawsonia inermis* to be partially or totally hydrolyzed enzymatically, to provide an aqueous solution containing lawsone;
b) adding an organic solvent to the solution obtained in step a), said organic solvent being selected from $C_4$-$C_{12}$ linear, or branched, alcohols to provide an aqueous phase and an organic phase;
c) collecting the organic phase obtained from step b); and
d) concentrating the organic phase collected in step c) to obtain a lawsone-rich extract.

Further aspects of the invention are as recited in the claims and/or described herein below.

DETAILED DESCRIPTION

The inventors of the present invention have developed a process for extracting *Lawsonia inermis* which allows obtaining a *Lawsonia inermis* extract with a high lawsone content via enzymatic hydrolysis of the glycosylated lawsone derivatives. The obtained extract exhibits great stability over time, in particular a stability which may be greater than the stability of known *Lawsonia inermis* extracts.

Process

The invention relates to a process for preparing a lawsone-rich extract which comprises the steps of:
a) macerating the aerial parts of *Lawsonia inermis* in water, at a pH ranging from 4 to 8 in order for the glycosylated lawsone derivatives, such as hennosides, initially present in the aerial parts of *Lawsonia inermis* to be partially or totally hydrolyzed enzymatically, to provide an aqueous solution containing lawsone;
b) adding an organic solvent to the solution obtained in step a), said organic solvent being selected from $C_4$-$C_{12}$ linear, or branched, alcohols to provide an aqueous phase and an organic phase;
c) collecting the organic phase obtained from step b); and
d) concentrating the organic phase collected in step c) to obtain a lawsone-rich extract.

The expression "lawsone-rich extract" as used herein means an extract containing from 7% to 60% by weight or from 7% to 50% by weight, in particular from 7% to 40% by weight of lawsone relative to the total weight of the dry extract (before any addition of a drying carrier—see below). Advantageously, the lawsone-rich extract contains at least 7%, preferably at least 8%, more advantageously at least 10% by weight of lawsone relative to the total weight of the dry extract (before any addition of a drying carrier).

The lawsone-rich extract typically contains more than 50% or more than 60%, advantageously more than 70% by weight of the lawsone initially present in the aerial parts of *Lawsonia inermis*, said lawsone being either in its free form or in the form of glycosylated derivatives, such as hennosides, in the aerial parts of *Lawsonia inermis*. The quantity of lawsone initially present in the aerial parts of *Lawsonia inermis* in its free form and in the form of glycosylated lawsone derivatives is also called the "plant lawsone potential." The process of the present invention may allow greater extraction of the plant lawsone potential versus known processes.

In some preferred embodiments of the process of the present invention, the lawsone-rich extract obtained in step d) contains from 50% to 90%, or from 60% to 90%, in particular from 70% to 90% of the lawsone potential of the plant. The lawsone potential of the plant can be determined according to the HPLC assay method described in the section following the example section (Method 1).

The term "aerial parts" as used herein designates the parts of the plant above the ground, for example, the leaves, petioles, flowers, seeds and branches, in particular leaves, branches and petioles, or a mix thereof, preferably leaves, branches or a mix thereof.

The term "glycosylated lawsone derivatives", also called lawsone glycosides or heterosides, as used herein refer to any compound of general formula (I):

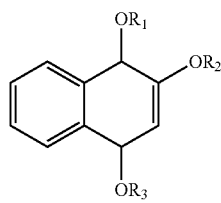

(I)

wherein $R_1$, $R_2$ and $R_3$ represent, independently, H or a sugar, such as glucose, at least one of $R_1$ to $R_3$ being different from H, for which hydrolysis of the glycoside bond(s) leads to the formation of aglycone which undergoes an autooxidation reaction to form lawsone. In particular, hennosides A, B and C are glycosylated lawsone derivatives.

The term "enzymatic hydrolysis" as used herein refers to a hydrolysis reaction catalyzed by an enzyme, which can be an endogenous *Lawsonia inermis* enzyme or an enzyme from an exogenous source, preferably an endogenous *Lawsonia inermis* enzyme, it being understood that said enzyme is a glucosidase, such as a β-glucosidase [Gallo et al.], whose action leads to breaking the glucoside bonds of the glycosylated lawsone derivatives.

Advantageously, the process of the invention does not include any step of changing the pH of the aqueous solution or the aqueous phase by addition of acid or base.

Step (a)

The aerial parts of *Lawsonia inermis* which are macerated are typically leaves or branches or mixtures thereof. The leaves may be fresh or dried, preferably dried. The aerial parts of *Lawsonia inermis* comprise glycosylated lawsone derivatives. The glycosylated lawsone derivatives are enzymatically hydrolyzed (partial or total hydrolysis) during the maceration step to provide to an aqueous solution comprising lawsone.

Step (a) is preferably conducted at a temperature ranging from 20° C. to 60° C., or from 20° C. to 50° C., in particular from 25° C. to 45° C., more particularly from 30° C. to 45° C., typically at about 40° C.

Step (a) is conducted at a pH ranging from 4 to 8. A pH ranging from 4 to 8 allows the enzyme or enzymes catalyzing the hydrolysis of the glycosylated lawsone derivatives to be functional. In some embodiments, step a) is conducted at pH ranging from 5 to 7.5, advantageously from 5.5 to 7.5, typically at neutral pH. "Neutral pH" means a pH comprised between 6.5 and 7.5, particularly around 7.

Step (a) is typically performed under stirring. Stirring may be done by any suitable methods known to the person skilled in the art.

The aerial parts of *Lawsonia inermis* are typically macerated for 15 minutes to 2 h, preferably for 15 minutes to 1 h, advantageously for about 30 minutes.

In some embodiments, step (a) is performed under stirring for 15 min to 2 h, preferably for 15 minutes to 1 h, advantageously for about 30 minutes.

The aerial parts of *Lawsonia inermis* are typically macerated in a volume of water whose weight is 2 to 15 times greater, advantageously 5 to 15 times greater, more advantageously 6 to 10 times greater, typically 10 times greater than the weight of the aerial parts of *Lawsonia inermis*. For instance, when the process according to the invention is implemented on 100 g of aerial parts of *Lawsonia inermis*, the volume of water used in step a) may range from 200 mL to 1500 mL, or from 500 mL to 1500 mL, advantageously from 600 mL to 1000 mL, typically is 1000 mL.

Step (b)

The organic solvent is added to the aqueous solution obtained in step a).

In some embodiments, the organic solvent is directly added to the aqueous solution obtained in step a). Then, the aqueous solution comprises the plant material and the macerating water. In these embodiments, it is to be understood that the organic solvent is directly added to the aqueous solution obtained in step a), i.e. no filtration step is performed between step a) and b).

In some embodiments, the process comprises a step of filtration between step a) and step b) allowing to separate the aerial parts of *Lawsonia inermis* from the aqueous solution containing lawsone. Alternatively, in some embodiments, the process comprises a step of filtration between step c) and step d) allowing to separate the aerial parts of *Lawsonia inermis* from the organic phase recovered/collected in step c).

The organic solvent which is added to the aqueous solution is selected from the group consisting of $C_4$-$C_{12}$ linear or branched alcohols and any mixtures thereof.

The term "alcohol" as used herein designates a compound of formula $R_4$—OH, wherein $R_4$ is a $C_4$-$C_{12}$ hydrocarbon chain.

The term "$C_4$-$C_{12}$ hydrocarbon chain" as used herein designates a linear or branched, saturated or unsaturated, preferably saturated, hydrocarbon chain comprising from 4 to 12 carbon atoms, preferably from 4 to 8 carbon atoms. Examples of "$C_4$-$C_{12}$ hydrocarbon chain" include, but are not limited to, butyl, pentyl, hexyl, heptyl, octyl, nonyl, decyl, undecyl, dodecyl, including any of their positional isomers.

In some embodiments, the organic solvent is $C_4$-$C_8$ linear or branched alcohols or any mixtures thereof.

The organic solvent is preferably selected from the group consisting of n-butanol, sec-butanol, isobutanol and any mixtures thereof. More preferably the organic solvent is n-butanol.

In a wish to provide processes that are greener and that allow claiming that the obtained extracts are natural, the solvent used in the present invention are preferably natural solvents and/or solvents of natural origin, i.e. obtained from renewable resources (as opposed to fossil resources). These solvents are advantageously obtainable by processes that respect the environment. Therefore, in some embodiments, the organic solvent is a biosourced solvent, more specifically a biosourced $C_4$-$C_{12}$ linear alcohol or a biosourced $C_4$-$C_{12}$ branched alcohol. In these embodiments, the extracts obtained according to the method of the invention, can qualify as natural extracts and/or extracts of natural origin, i.e. coming from renewable resources, as opposed to fossil resources.

The use of alcohols in the present invention present many advantages, in particular during recycling of the solvent at industrial level. Alcohols do not degrade during recycling operations, unlike esters, e.g. ethylacetate or isopropylacetate, or certain ketones, in particular acetone. Furthermore, the presence of residual water in the solvent does not pose any recycling implementation problem. Recycling is facilitated by alcohols.

Step b) may be performed batchwise or continuously.

In some particular batchwise embodiments, step b) of the process according to the invention comprises the following 3 substeps:
b.1) adding an organic solvent to the aqueous solution obtained in step a), said organic solvent being a $C_4$-$C_{12}$ linear alcohol, a $C_4$-$C_{12}$ branched alcohol or a mixture thereof;
b.2) stirring the solution obtained in step b.1) for 15 minutes to 2 h, in particular for 15 minutes to 1 h, typically for about 30 minutes; and
b.3) decantating the mixture obtained in b.2), until two distinct phases are obtained, i.e. an aqueous phase and an organic phase.

Thus, the succession of substeps b.1), b.2) and b.3) leads to the formation of an aqueous phase and an organic phase.

The volume of organic solvent added during step b), in particular during step b.1), is such that the volume ratio of said organic solvent added during b) to the volume of water used during step a) is comprised between 0.25 and 2, notably between 0.5 and 2, notably between 0.8 and 1.5, in particular between 1 and 1.3.

Steps c) and d) and Further Optional Steps

The organic phase obtained after performing step b) is collected and then concentrated.

The aqueous phase obtained after performing step b) is typically discarded. However, it will be readily understood that step b) may be repeated at least once. Thus, in a second step b), an organic solvent as disclosed herein may be added to the aqueous phase collected after performing a first step b). The organic phase obtained after performing the second step b) is collected and combined with the organic phase obtained after performing the first step b). The combined organic phases are then concentrated.

In some embodiments, the process according to the present invention comprises several iterations, e.g. from 2 to 5, of step b) followed by step c). The process then comprises as step d) the step of concentrating the combination of organic phases recovered from several iterations of step b) followed by step c).

Advantageously, the lawsone-rich extract obtained in step d) contains more than 50% or more than 60%, advantageously more than 70% of the lawsone initially present in the aerial parts of Lawsonia inermis, said lawsone being either in its free form or in the form of glycosylated derivatives, such as hennosides, in the aerial parts of Lawsonia inermis.

Advantageously, the lawsone-rich extract obtained in step d) contains from 7 to 60% by weight of lawsone relative to the total weight of the dry extract and further comprises luteolin, apigenin and 2,3,4,6-tetrahydroxyacetophenone.

Advantageously, the lawsone-rich extract obtained in step d) further comprises coumaric acid and/or glycosylated luteolin, in particular luteolin-6-C-neohesperidoside.

Advantageously, the lawsone-rich extract obtained in step d) do not comprise more than 2% by weight of proteins, peptides or amino acids relative to the total weight of the dry extract.

In some embodiments, the process according to the present invention further comprises the step of drying the lawsone-rich extract obtained in step d) (step e)). A dry lawsone-rich extract is thus obtained. Drying may be performed according to methods well known to a person skilled in the art. In particular, the drying step may be done by pallet dryer, vacuum drying, atomization, microwaves, zeodration or lyophilization.

The term "dry extract" as used herein designates an extract with no extraction solvent or medium, or containing them only in insignificant trace amount. Such a dry extract thus contains only the material coming from Lawsonia inermis.

Advantageously, the dry lawsone-rich extract obtained in step e) contains from 0.6 to 1.4% by weight of lawsone relative to the total weight of the dry extract and further comprises luteolin, apigenin and 2,3,4,6-tetrahydroxyacetophenone.

Advantageously, the dry lawsone-rich extract obtained in step e) further contains, relative to the total weight of the dry extract:
from 0.05 to 1.0% by weight of luteolin,
from 0.01 to 0.5% by weight of apigenin, and
from 0.05 to 1.0% by weight of 2,3,4,6-tetrahydroxyacetophenone.

In some embodiments, the process according to the present invention further comprises a step c') of adding a carrier (as defined herein below) between step c) and d), and a step e) of drying after step d). Step e) may be performed as disclosed herein above. A standardized dry lawsone-rich extract is thus obtained.

In some embodiments, the process according to the invention further comprises a step of extracting pigments, also called decoloration step. The pigments extracted during the decoloration step are notably chlorophylls. It is to be understood that lawsone is not part of the pigments that the decoloration step seeks to eliminate.

The pigments may be extracted with an organic solvent. It is readily understood that the organic solvent is a solvent that does not solubilize lawsone well. Thus, the solubility of lawsone in the organic solvent step used for the decoloration step is less than 15%, notably less than 10%, advantageously less than 5% by weight at 25° C.; the percentages being expressed relative to the total weight of lawsone contained in the extract or the solution which is undergoing the decoloration step. Preferably, an organic solvent in which the lawsone is not soluble is used in the decoloration step. Advantageously, said organic solvent is a saturated or unsaturated hydrocarbon. The term "saturated or unsaturated hydrocarbon" means a compound made up uniquely of hydrogen and carbon atoms. In some embodiments, the saturated hydrocarbon is selected in the group consisting of pentane, hexane, heptane, nonane, decane and cyclohexane. In some embodiments, the unsaturated hydrocarbon is benzene.

Preferably, the decoloration step, to extract pigments, such as chlorophyll, is performed using heptane as organic solvent.

The pigment extraction step done with an organic solvent may consist in a liquid-liquid or liquid-solid extraction.

When the pigment extraction step is a liquid-liquid extraction, said step is performed between steps a) and b) of the process of the invention.

Advantageously, the liquid-liquid pigments extraction step using an organic solvent comprises the following 4 substeps:
  i) adding an organic solvent as disclosed above to the aqueous solution obtained from step a),
  ii) stirring the solution obtained from step i) for 15 minutes to 2 h, in particular for 15 minutes to 1 h, typically for about 30 minutes,
  iii) decantating the mixture obtained from step ii), until two distinct phases are obtained, i.e., an aqueous phase and an organic phase, and
  iv) eliminating of the organic phase.

Step b) of the process of the invention is then implemented on the aqueous phase resulting from step iii).

When the pigment extraction step is a liquid-solid extraction, the liquid-solid pigments extraction step follows drying step e) of the process of the invention. Liquid-solid extraction may be done according to methods well known to the skilled person.

Alternatively, the decoloration step may be done using supercritical $CO_2$, with or without the addition of co-solvent, directly in the dry extract. The chlorophyll is entrained by the supercritical $CO_2$. The residue is the decolored dry extract.

In some embodiments, the process of the invention further comprises a filtration step between step a) and b), in order to separate the aerial parts of *Lawsonia inermis* from the aqueous solution containing lawsone or between step c) and d), in order to separate the aerial parts of *Lawsonia inermis* from the organic phase resulting from step c).

In some embodiments, a pectinase-type enzyme may be added in step a).

The process according to the invention may also be applied to any other plant that contains lawsone, such as *Impatiens balsamina*. The skilled person will know how to adapt the method of the invention to the plant in question. Thus, in the case of *Impatiens balsamina*, the skilled person will do an extraction of the roots, the parts of *Impatiens balsamina* richest in lawsone.

*Lawsonia inermis* Extract

The invention as disclosed herein allows preparing an extract of the aerial parts of *Lawsonia inermis*, in particular an extract of leaves and/or branches of *Lawsonia inermis*, with a high lawsone content. The lawsone content of said extract is stable over time.

In one aspect, the invention relates to an extract of the aerial parts of *Lawsonia inermis*, in particular an extract of leaves and/or branches of *Lawsonia inermis*, containing from 7 to 60% by weight of lawsone relative to the total weight of the dry extract, wherein the lawsone results from enzymatic hydrolysis of glycosylated lawsone derivatives, such as hennosides, and wherein the lawsone content of the extract is stable over time in said extract.

In a second aspect, the invention also relates to an extract of the aerial parts of *Lawsonia inermis*, in particular an extract of leaves and/or branches of *Lawsonia inermis* that can be obtained by the process disclosed herein. The extract contains from 7 to 60% by weight of lawsone relative to the total weight of the dry extract, wherein the lawsone results from enzymatic hydrolysis of glycosylated lawsone derivatives, such as hennosides, wherein the lawsone content of the extract is stable over time.

The extracts of the aerial parts of *Lawsonia inermis* according to first or second aspect of the present invention are as disclosed herein below.

The lawsone content of an extract as disclosed herein is considered to be "stable over time" when the quantity of lawsone initially present in the extract does not decrease by more than 50%, advantageously not more than 40%, in particular not more than 30%, advantageously not more than 20%, notably not more than 15%, advantageously not more than 10% in 1 month at room temperature (15° C.-25° C.), with a relative humidity (RH) of 60%, and protected from light. The room temperature values are those defined in the European Pharmacopoeia.

In some embodiments, the lawsone content of an extract as disclosed herein does not decrease by more than 50%, advantageously not more than 40%, in particular not more than 30%, advantageously not more than 20%, even more advantageously not more than 15% or 10%, in 3 months under the previously enumerated conditions.

Advantageously, the lawsone content of an extract as disclosed herein does not decrease by more than 50%, advantageously not more than 40%, in particular not more than 30%, advantageously not more than 20%, even more advantageously not more than 15% or 10%, in 6 months under the previously enumerated conditions.

Preferably, the lawsone content of an extract as disclosed herein does not decrease by more than 50%, advantageously not more than 40%, in particular not more than 30%, advantageously not more than 20%, even more advantageously not more than 15% or 10%, in 12 months at room temperature under the previously enumerated conditions.

The stability of an extract as disclosed herein may also be evaluated under so-called accelerated stability conditions. These conditions are a temperature of 40° C. (±2) and an RH of 75% (±5). The lawsone content of an extract as disclosed herein is evaluated as being "stable over time" under accelerated stability conditions if the quantity of lawsone initially present in the extract does not decrease by more than 50%, advantageously not more than 40%, in particular not more than 30%, advantageously not more than 20%, even more advantageously not more than 10%, in 1 month.

Advantageously, the lawsone content of an extract as disclosed herein does not decrease by more than 50%, advantageously not more than 40%, in particular not more than 30%, advantageously not more than 20%, even more advantageously not more than 10%, in 3 months under the previously enumerated accelerated stability conditions. In particular, the lawsone content of an extract as disclosed herein does not decrease by more than 50%, advantageously not more than 40%, in particular not more than 30%, advantageously not more than 20%, even more advantageously not more than 10%, in 6 months under the previously enumerated accelerated stability conditions.

The extract according as disclosed herein contains from 7% to 60%, in particular from 7% to 50% or from 7 to 40% by weight of lawsone relative to the total weight of the dry extract. Advantageously, the extract as disclosed herein contains at least 7%, advantageously at least 8%, preferably at least 10%, more advantageously at least 15% by weight of lawsone relative to the total weight of the dry extract; the percentages being expressed relative to the total weight of the dry extract (before any addition of a drying carrier). In some embodiments, extract as disclosed herein contains from 15% to 40% by weight of lawsone relative to the total weight of the dry extract. The lawsone content can be determined according to the HPLC assay method described in the following examples (Method 1).

In some embodiments, an extract as disclosed herein does not contain more than 2%, preferably not more than 1.5%, notably not more than 1%, by weight of proteins, peptides or amino acids relative to the total weight of the dry extract, advantageously from 0 to 1%, more advantageously from 0.1 to 1%, by weight of proteins, peptides or amino acids relative to the total weight of the dry extract.

The free amino acids, peptides and proteins can be assayed by ninhydrin spectrophotometry, according to the method described in the following examples (Method 2).

In some embodiments, an extract as disclosed herein also comprises chlorophylls, in particular chlorophyll a and/or chlorophyll b, the total chlorophyll content being less than 25% by weight relative to the total weight of the dry extract, notably less than 20% by weight, advantageously less than 10% by weight relative to the dry extract.

In some embodiments, the extract as disclosed herein does not contain more than 5%, preferably not more than 2% by weight of chlorophylls relative to the total weight of the dry extract. Advantageously, the extract as disclosed herein does not contain chlorophyll. The chlorophylls can be assayed by weight assay according to the method described in the following examples (method 3).

An extract as disclosed herein may also contain any compound naturally present in the aerial parts of *Lawsonia inermis*, in particular in the leaves and or branches of *Lawsonia inermis*.

In some embodiments, an extract as disclosed herein also contains:
- phenol compounds, such as gallic acid, coumaric acid, 2,3,4,6-tetrahydroxyacetophenone and 3,4,5-trihydroxyacetophenone;
- flavonoids, such as luteolin, apigenin, catechin, 3%4%5,7-tetrahydroxyflavanone, 3',5,7-trihydroxy-4'-methylflavone;
- sterols, such as β-sitosterol;
- triterpenes, such as lupeol; and/or
- heterosides thereof, such as lalioside, myrciaphenone A, 1,2-dihydroxy-4-O-glycosyloxynaphtalene (also called 4-O-β-D-glucopyranoside), luteolin-4'-O-glucoside, apigenin-7-O-β-glucoside, luteolin-3'-O-glucoside, apigenin-4'-O-β-glucoside and luteolin-6-C-neohesperidoside.

More particularly, an extract as disclosed herein also contains:
- phenol compounds, such as gallic acid, coumaric acid, 2,3,4,6-tetrahydroxyacetophenone and 3,4,5-trihydroxyacetophenone;
- flavonoids, such as luteolin, apigenin, catechin, 3',4',5,7-tetrahydroxyflavanone, 3',5,7-trihydroxy-4'-methylflavone; and/or
- heterosides thereof, such as lalioside, myrciaphenone A, 1,2-dihydroxy-4-O-glycosyloxynaphtalene, luteolin-4'-O-glucoside, apigenin-7-O-β-glucoside, luteolin-3'-O-glucoside, apigenin-4'-O-β-glucoside and luteolin-6-C-neohesperidoside.

The chemical structures of the above specific compounds are indicated in the following Table 1:

TABLE 1 compounds potentially present in the extract of the invention

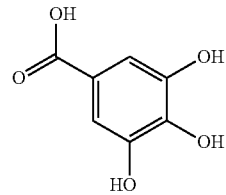 [SMILES: O=C(O)c1cc(O)c(O)c(O)c1]

Chemical Formula: $C_7H_6O_5$
Molecular Weight: 170,1200
gallic acid

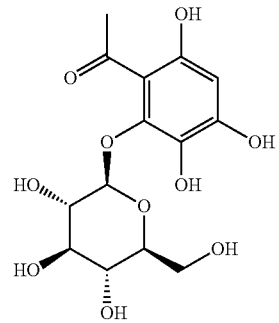 [SMILES: CC(=O)c1c(O)cc(O)c(O)c1O[C@H]1O[C@@H](CO)[C@H](O)[C@@H](O)[C@@H]1O]

Chemical Formula: $C_{14}H_{18}O_{10}$
Molecular Weight: 346,2880
lalioside

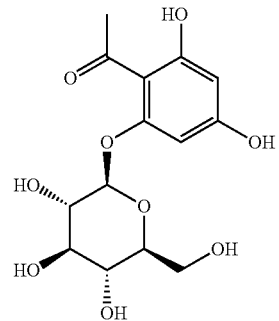 [SMILES: CC(=O)c1c(O)cc(O)cc1O[C@H]1O[C@@H](CO)[C@H](O)[C@@H](O)[C@@H]1O]

Chemical Formula: $C_{14}H_{18}O_9$
Molecular Weight: 330,2890
myrciaphenone A

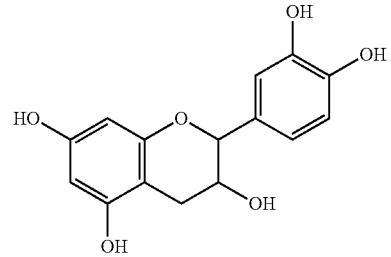 [SMILES: Oc1cc(O)c2c(c1)OC(c1ccc(O)c(O)c1)C(O)C2]

Chemical Formula: $C_{15}H_{14}O_6$
Molecular Weight: 290,2710
catechin

TABLE 1-continued compounds potentially present in the extract of the invention

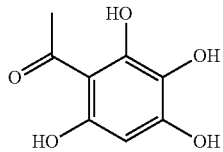

Chemical Formula: $C_8H_8O_5$
Molecular Weight: 184,1470
2,3,4,6-tetrahydroxyacetophenone

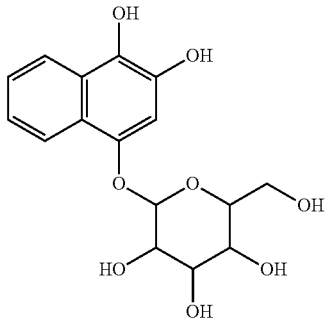 [SMILES: OCC1OC(Oc2cc(O)c(O)c3ccccc23)C(O)C(O)C1O]

Chemical Formula: $C_{16}H_{18}O_8$
Molecular Weight: 338,3120
1,2-dihydroxy-4-O-glycosyloxynaphtalene

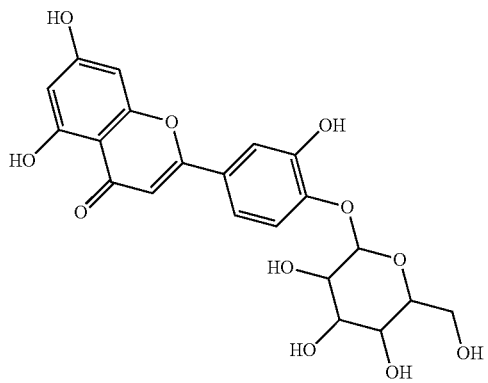 [SMILES: O=c1cc(-c2ccc(OC3OC(CO)C(O)C(O)C3O)c(O)c2)oc2cc(O)cc(O)c12]

Chemical Formula: $C_{21}H_{20}O_{11}$
Molecular Weight: 448,3800
luteolin-4'-O-glucoside

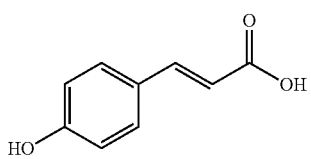

Chemical Formula: $C_9H_8O_3$
Exact Mass: 164,0473
para-coumaric acid

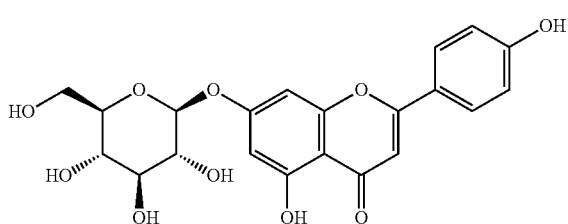 [SMILES: O=c1cc(-c2ccc(O)cc2)oc2cc(O[C@@H]3O[C@H](CO)[C@@H](O)[C@H](O)[C@H]3O)cc(O)c12]

TABLE 1-continued compounds potentially present in the extract of the invention

Chemical Formula: $C_{21}H_{20}O_{10}$
Exact Mass: 432,1056
apigenin-7-O-β-glucoside

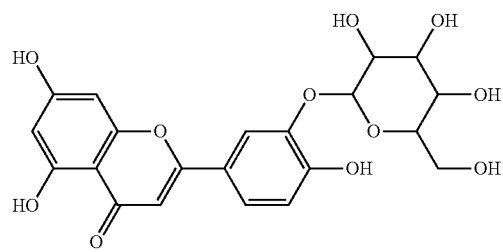 [SMILES: O=c1cc(-c2ccc(O)c(OC3OC(CO)C(O)C(O)C3O)c2)oc2cc(O)cc(O)c12]

Chemical Formula: $C_{21}H_{20}O_{11}$
Molecular Weight: 448,3800
luteolin-3'-O-glucoside

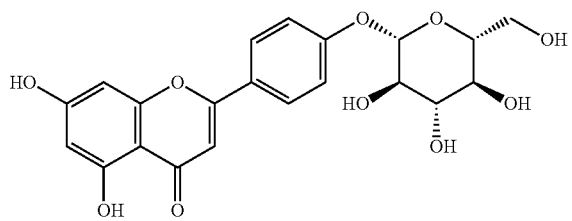 [SMILES: O=c1cc(-c2ccc(O[C@@H]3O[C@H](CO)[C@@H](O)[C@H](O)[C@H]3O)cc2)oc2cc(O)cc(O)c12]

Chemical Formula: $C_{21}H_{20}O_{10}$
Exact Mass: 432,1056
apigenin-4'-O-β-glucoside

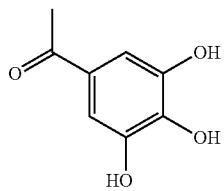

Chemical Formula: $C_8H_8O_4$
Molecular Weight: 168,1480
3,4,5-trihydroxyacetophenone

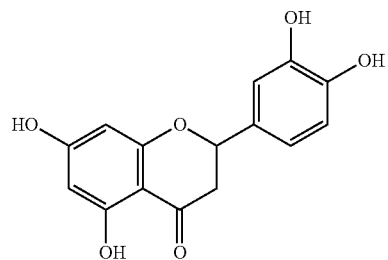 [SMILES: O=C1CC(c2ccc(O)c(O)c2)Oc2cc(O)cc(O)c21]

Chemical Formula: $C_{15}H_{12}O_6$
Molecular Weight: 288,2550
3',4',5,7-tetrahydroxyflavanone

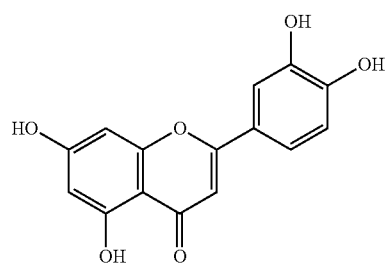 [SMILES: O=c1cc(-c2ccc(O)c(O)c2)oc2cc(O)cc(O)c12]

TABLE 1-continued compounds potentially present in the extract of the invention Chemical Formula: C₁₅H₁₀O₆
Molecular Weight: 286,2390
luteolin

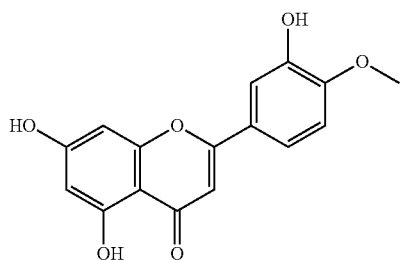 [SMILES: COc1ccc(-c2cc(=O)c3c(O)cc(O)cc3o2)cc1O]

Chemical Formula: C₁₆H₁₂O₆
Molecular Weight: 300,2660
3',5,7-trihydroxy-4'-methylflavone

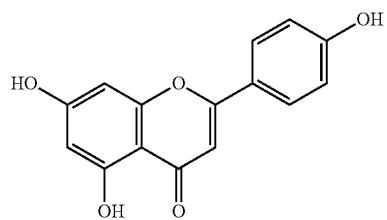 [SMILES: O=c1cc(-c2ccc(O)cc2)oc2cc(O)cc(O)c12]

Chemical Formula: C₁₅H₁₀O₅
Exact Mass: 270,0528
apigenin

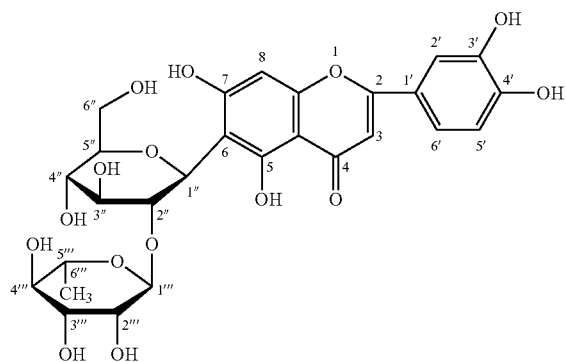

luteolin-6-C-neohesperidoside

Flavonoids, such as luteolin and apigenin have many interesting biological properties, such as free radical scavenging and antioxidative effects [Romanov et al., *Neoplasma* 2001, 48(2), 104-107] as well as anti-inflammatory activity, which, combined with their capacity to absorb UV light, are responsible for their ability to provide protection from UV radiation [Saewan et al., *JAPS* 2013, 3(9), 129-141]. Although the hair photoprotection is a topic that is not commonly addressed, the chemical effects of UV radiation and their impact on the hair shaft should not be neglected [Draelos, *Dermatol. Clin.* 2006, 24, 81-84]. Therefore, the presence of compounds that have a photoprotective effect in a cosmetic composition intended for hair dyeing is of particular interest.

Luteolin and apigenin are also well-known natural dyes, that can be used for coloring hair and textiles.

Besides, it has been shown that apigenin is a hair-growth-promoting agent [Huh et al. *Arch. Dermatol. Res.*, 2009, 301, 381-385].

Polyphenols, such as 2,3,4,6-tetrahydroxyacetophenone, and phenolic acids, such as para-coumaric acid, also have antioxidant and photoprotective properties [Nichols et al., *Arch. Dermatol. Res.* 2010, 302, 71-83].

In some embodiments, an extract as disclosed herein contains from 1% to 40%, in particular from 2% to 30% by weight of phenol compounds with respect to the total weight of the dry extract. The phenol compounds content can be determined by spectrophotometry in accordance with the method described herein (method 4).

In some embodiments, an extract as disclosed herein does not contain more than 5% by weight of saccharides relative to the total weight of the dry extract, advantageously from 0.1 to 5%, more advantageously from 0.5 to 5%, by weight of saccharides relative to the total weight of the dry extract. The saccharides content can be determined by colorimetric assay with dinitrosalicylic in accordance with the method described herein (method 5).

Thus, more specifically, the extract of the aerial parts of *Lawsonia inermis*, in particular an extract of leaves and/or branches of *Lawsonia inermis*, contains from 7 to 60% by weight of lawsone relative to the total weight of the dry extract, wherein the lawsone results from enzymatic hydrolysis of glycosylated lawsone derivatives, such as hennosides, wherein said extract further comprises luteolin, apigenin and 2,3,4,6-tetrahydroxyacetophenone.

The extract as disclosed herein may further comprise coumaric acid, in particular para-coumaric acid.

The extract as disclosed herein may further comprise 3,4,5-trihydroxyacetophenone and/or 1,2-dihydroxy-4-O-glycosyloxynaphtalene.

The extract as disclosed herein may further comprise glycosylated luteolin, in particular luteolin-6-C-neohesperidoside.

In some embodiments, the extract of the aerial parts of *Lawsonia inermis*, in particular an extract of leaves and/or branches of *Lawsonia inermis*, containing from 7 to 60% by weight of lawsone relative to the total weight of the dry extract, wherein the lawsone results from enzymatic hydrolysis of glycosylated lawsone derivatives, such as hennosides, further comprises 2,3,4,6-tetrahydroxyacetophenone.

In some embodiments, the extract as disclosed herein may be in the dry extract form, advantageously in the powder form.

In some embodiments, the extract as disclosed herein may be a standardized extract.

"Standardized extract" means an extract having a desired/chosen lawsone content. For instance, for a cosmetic application, the lawsone content in the extract may range from 0.6% to 1.4%, advantageously from 1 to 1.3%, in particular approximately 1.3% by weight of lawsone relative to the total weight of the dry extract.

This lawsone content may be obtained by the addition of a carrier, chosen from among protein-free carriers alone or in mixture.

Said "carrier" must be inert vis-à-vis the extract and its components: it does not interact with the extract nor its components, more particularly with lawsone, contributes to its protection and allows to standardize the final content of the active extract or molecule. It must be "cosmetically-acceptable", which means, in the context of the present invention, that it is useful in the preparation of a cosmetic composition, and generally safe, non-toxic and neither biologically nor otherwise undesirable, and that is acceptable for a cosmetic use, notably by topical application.

The carrier can be chosen from among propanediol, pentanediol, glycerine, propylene glycol, methyl THF and amylic alcohol.

A dry extract according to the invention can also be standardized.

For dry extracts, the carrier may act as a support during the drying of the extract, and is preferably chosen from among sugars and polysaccharide derivatives, such as fructose, glucose, sucrose, maltodextrins, cellulose derivatives, starch, notably maize, wheat or rice starch, agar-agar, gums, mucilages; and polyols such as mannitol, sorbitol, xylitol, etc. In particular, it is selected from fructose, maltodextrins and starch, notably rice starch.

Within the framework of the present invention, the carrier is preferably a natural carrier and/or of natural origin from renewable resources, as opposed to fossil resources, these carriers advantageously being obtainable by processes that respect the environment.

The invention relates more particularly to a standardized dry extract of aerial parts of *Lawsonia inermis* containing from 0.6 to 1.4 wt. % of lawsone, advantageously from 1 to 1.3 wt. %, more particularly about 1.3 wt. % of lawsone relative to the total weight of the dry extract and wherein said extract further contains luteolin, apigenin and 2,3,4,6-tetrahydroxyacetophenone. The extract may further comprise 3,4,5-trihydroxyacetophenone and/or 1,2-dihydroxy-4-O-glycosyloxynaphtalene.

The invention relates more particularly to a standardized dry extract of aerial parts of *Lawsonia inermis* containing from 0.6 to 1.4 wt. % of lawsone, advantageously from 1 to 1.3 wt. %, more particularly about 1.3 wt. % of lawsone relative to the total weight of the dry extract and wherein said extract further contains 2,3,4,6-tetrahydroxyacetophenone. The extract may further comprise 3,4,5-trihydroxyacetophenone and/or 1,2-dihydroxy-4-O-glycosyloxynaphtalene.

The standardized dry extracts as disclosed herein may further comprise coumaric acid, in particular para-coumaric acid.

The standardized dry extracts as disclosed herein may further comprise glycosylated luteolin, in particular luteolin-6-C-neohesperidoside.

The standardized dry extracts as disclosed herein may further comprise any of the compounds disclosed in table 1.

In particular, the standardized dry extract as disclosed herein is characterized by one or more of the following features, advantageously by all of them (weight % is expressed relative to the total weight of the standardized dry extract):

the standardized dry extract comprises from 0.6 to 1.4%, advantageously from 1 to 1.3% by weigh of lawsone;
the standardized dry extract comprises from 0.2 to 3.0% by weigh of phenol compounds;
the standardized dry extract comprises from 0.05 to 1.0 wt. % of luteolin;
the standardized dry extract comprises from 0.01 to 0.5 wt. % of apigenin;
the standardized dry extract comprises from 0.05 to 1.0 wt. % of 2,3,4,6-tetrahydroxyacetophenone;
the standardized dry extract comprises from 0.01 to 0.1 wt. % of coumaric acid, in particular para-coumaric acid;
the standardized dry extract comprises glycosylated luteolin, in particular luteolin-6-C-neohesperidoside;
the standardized dry extract does not comprise more than 0.2 wt. % of proteins, peptides or amino acids, advantageously it comprises from 0 to 0.2 wt. %, advantageously from 0.01 to 0.2 wt. % of proteins, peptides or amino acids;
the standardized dry extract does not comprise chlorophylls;
the standardized dry extract does not comprise more than 0.5 wt. % of saccharide compounds, advantageously it comprises from 0.01 to 0.5 wt. %, advantageously from 0.05 to 0.5 wt. % of saccharide compounds.

Preferably, the standardized dry extract complies with the specifications defined herein above regarding the stability of the lawsone content over time, including stability under accelerated conditions.

Thus, after 1 month, 3 months, 6 months or 12 months at room temperature (15° C.-25° C.), with a relative humidity (RH) of 60%, and protected from light, or after 1 month, 3 months, 6 months at 40° C. (±2° C.), with a relative humidity (RH) of 75% (±5° C.), the lawsone content does not decrease by more than 50%, advantageously by not more than 40%, in particular not more than 30%, advantageously not more than 20%, notably not more than 15%, advantageously not more than 10%, more advantageously not more than 5%.

In some embodiments, the standardized dry extract comprises at least 80 wt. %, advantageously at least 90 wt. %, in particular at least 92 wt. % of carrier relative to the total weight of the standardized dry extract.

Compositions

The invention also relates to a composition, in particular a cosmetic dye composition, comprising an extract or a standardized dry extract as disclosed herein, and, if applicable, an appropriate excipient.

In some embodiments, the invention relates to a composition, in particular a cosmetic dye composition, comprising an extract or standardized dry extract as disclosed herein that further comprises luteolin, apigenin and 2,3,4,6-tetrahydroxyacetophenone. The extract may further comprise 3,4,5-trihydroxyacetophenone and/or 1,2-dihydroxy-4-O-glycosyloxynaphtalene.

In some embodiments, the invention relates to a composition, in particular a cosmetic dye composition, comprising an extract or standardized dry extract as disclosed herein that further comprises coumaric acid and luteolin-6-C-neohesperidoside. The extract may further comprise 3,4,5-trihydroxyacetophenone and/or 1,2-dihydroxy-4-O-glycosyloxynaphtalene Said composition is preferably formulated to be suitable for use as dyeing composition, in particular to be administered externally and topically for a cosmetic composition. The composition as disclosed herein may be formulated in the form of different preparations suited to topical administration for cosmetic compositions or external administration and notably including creams, emulsions, milks, ointments, lotions, oils, aqueous or water-alcohol or glycolic solutions, powders, sprays, shampoos, varnishes or any other product for external application.

The composition is free of the stabilizers usually present in henna compositions to stabilize lawsone.

The composition as disclosed herein is advantageously free of additives consisting of synthetic dyes, such as diaminotoluenes and diaminobenzenes, in particular PPD (para-diphenylenediamine) which is the most used, or heavy metals [Wang et al. *J. environ. Anal. Toxicol.* 2016, 6(3); Wang et al. *J. Chromatogr. B* 2011, 879, 1795-1801].

The composition is advantageously a cosmetic dye composition, comprising at least one cosmetically-acceptable excipient.

The term "cosmetically-acceptable excipient" as used herein means an excipient that is useful in the preparation of a cosmetic composition, which is generally safe, non-toxic and neither biologically nor otherwise undesirable and which is acceptable for a cosmetic use, notably by topical application.

The composition as disclosed herein may comprise at least one cosmetically-acceptable excipient chosen from among surfactants, thickeners, preservatives, fragrances, dyes, chemical or mineral filters, moisturizers, thermal waters, etc. The skilled person knows to adjust the formulation of the composition according to the invention by using their general knowledge.

In some embodiments, the composition, in particular the cosmetic dye composition, comprises from 0.01 to 50%, notably from 1 to 40%, in particular from 2 to 30% by weight of the extract as disclosed herein, the weight of the extract being expressed in dry extract relative to the total weight of the composition.

In some embodiments, the composition, in particular the cosmetic dye composition, comprises from 1 to 20%, notably from 5 to 20%, in particular from 10 to 20% by weight of the standardized extract as disclosed herein, the weight of the standardized extract being expressed in dry extract relative to the total weight of the composition.

Preferably, the composition, in particular the cosmetic dye composition has a lawsone content ranging from 0.2% to 2%, notably from 0.5 to 1.5% by weight of lawsone relative to the total weight of the composition.

In particular, the composition, in particular the cosmetic dye composition has a lawsone content ranging from 1.0% to 1.3% by weight, or of approximately 1.3% by weight, with regard to the total weight of the composition.

This lawsone content may be obtained by the addition of a carrier, chosen from among protein-free carriers alone or in mixture. The carrier can notably be chosen from among propanediol, pentanediol, glycerine, propylene glycol, methyl THF and amylic alcohol.

When the cosmetic dye composition is in powder form, the carrier is preferably chosen from among sugars and polysaccharide derivatives, such as fructose, glucose, sucrose, maltodextrins, cellulose derivatives, starch, notably maize, wheat or rice starch, agar-agar, gums, mucilages; and polyols such as mannitol, sorbitol, xylitol, etc. The carrier is typically fructose, maltodextrine or starch, in particular rice starch.

When the composition, in particular the cosmetic dye composition, is in the powder form, the skilled person can adjust its particle size by any method well known to them.

In particular, a cosmetic dye composition may be in the form of powder, with a particle size less than 250 μm.

Preferably, the composition, in particular a cosmetic dye composition, does not contain more than 2% by weight of proteins, peptides or amino acids relative to the total weight of the dry extract.

The composition, in particular the cosmetic dye composition may also comprise one or more additional dye(s) and/or pigment(s).

It is understood that the lawsone content of a composition is stable over time.

Thus, after 1 month, 3 months, 6 months or 12 months at room temperature (15° C.-25° C.), with a relative humidity (RH) of 60%, and protected from light, the lawsone content of said extract does not decrease by more than 60%, in particular by not more than 50%, preferably by not more than 40%, advantageously by not more than 30%, in particular not more than 20%, notably not more than 15%, advantageously not more than 10%.

The present invention also concerns a cosmetic method for dying keratin fibers comprising the application of a composition according to the invention onto keratin fibers, optionally followed by rinsing.

"Keratin fibers" means the keratin present in the epidermis and hair and nails.

The present invention also concerns a method for tattooing the skin.

The present invention also has for a subject a textile or furniture dye comprising an extract according to the invention. Such a dye may also comprise one or more additional dye(s) and/or pigment(s). The dye according to the present invention may also comprise any adjuvant known to the skilled person, who knows how to adjust the formulation of the dye according to the invention by using their general knowledge. The present invention also relates to a use of such a dye for dying textile or wood fibers.

The present invention also relates to a vegetable ink comprising an extract as disclosed herein or a composition as disclosed herein. The ink may comprise suitable excipients, such as oils, resins and mixtures thereof.

FIGURE

The Figure represents the normalized UHPLC-UV chromatogram of an extract obtained in accordance with the process of example 1.

The following example illustrates the invention.

EXAMPLE 1

50 g of uncrushed leaves of *Lawsonia inermis* are extracted by 6 volumes of water at 30-40° C. for 30 min. Six volumes of n-butanol are added to this solution at room temperature. This mixture is stirred for 30 min. After decantation, the upper butanol phase is recovered, the aqueous phase being separated because it is practically free of lawsone. The organic phase is concentrated with passage over water.

The lawsone content in the organic phase is determined by HPLC. Maltodextrin is added in an amount sufficient to obtain a mixture comprising from 1.1 to 1.3 wt. % of lawsone.

The concentrate is dried to obtain a powder.

Characterization

A) Structural Analysis

Material Et Methods

Chromatographic separations were performed on a Waters ACQUITY UHPLC system equipped with a quaternary pump, an auto-sample injector, an on-line degasser, an automatic thermostatic column oven and a DAD detector (200-500 nm). An ACQUITY UPLC BEH Shield RP18 column (100 mm×2.1, 1.7 μm) equipped with a Vanguard™ precolumn (5 mm×2.1) (Waters Corporation, Milford, USA) at 35° C. was used and the flow rate was set at 0.4 mL/min. The mobile phase consisted of a linear gradient system of (A) water with 0.1% formic acid and (B) acetonitrile and (C) methanol as wash solvent: 0-9 min, 2%-100% B; 9-9.55 min, maintain 100% B; 9.55-9.70 min, 0%-100% C; 9.7-10.2 min, maintain 100% C; 10.20-10.35 min, 0%-100% B; 10.35-10.85 min, maintain 100% B; 10.85-11 min, 0%-98% A; held at 98% A-2% B for 1 min for equilibration of the column.

Compounds were identified by high-resolution mass spectrometry, 1D- and 2D-NMR experiments ($^1$H NMR, $^{13}$C NMR, DEPT, COSY, HMBC, HSQC).

Results

UHPLC-UV Chromatogram

The obtained UHPLC-UV chromatogram is displayed in the Figure. The peaks that can be observed have been associated with the following compounds:

| Resolution time | Compound |
| --- | --- |
| 4.47 | lawsone |
| 3.38 | 2,3,4,6-tetrahydroxyacetophenone |
| 5.34 | luteolin |
| 5.96 | apigenin |

The presence of glycosylated luteolin, in particular of luteolin-6-C-neohesperidoside and coumaric acid, is noted.

B) Quantitative Analysis: Experimental Conditions

Luteolin, apigenin were titrated by analytical HPLC performed with a C18 column (XBridge 100 C18; 3.5 mm, 150 mm×4.6 mm) using gradient conditions (see below) with $H_2O$/trifluoroacetic acid 0.1% (A) and Acetonitrile/trifluoroacetic acid 0.1% (B) as eluent:

Gradient conditions: t0 A 18% B 82%; t1 min: A 18% B 82%; 10 min A 50% B 50%; 10.1 min: A 18% B 82%

UV detection is at 340 nm for apigenin and 310 nm for luteolin. Flow rate was 1 mL/min and temperature 40° C. Pure luteolin, apigenin and p-coumarin were used for calibration.

Method 1: Lawsone Assay by HPLC

This method can be applied for:

A. the assay of lawsone in an extract

B. the assay of the total lawsone present in the free form or form of glycosylated lawsone derivatives in the aerial parts of *Lawsonia inermis*, obtained by acid hydrolysis, and thus quantifying the lawsone potential in the plant, C. the assay of the lawsone formed by enzymes.

Reagents

Lawsone>97% (HPLC) SIGMA—ref: H46805

Dichloromethane for analyses.

Sulfuric acid for analyses.

Methanol for analyses.

HPLC-grade water.

HPLC-grade acetonitrile.

HPLC-grade trifluoroacetic acid.

HPLC Conditions

Column: XBridge C18, 3.5 μm, 4.6×150 mm Waters

Furnace: 40° C.

Solvents: S-A: 0.1% trifluoroacetic acid in water.

S-B: 0.1% trifluoroacetic acid in acetonitrile.

Gradient: T0 min 40% S-A; T 1 min 40% S-A; T 10 min 5% S-A; T 11 min 5% S-A; T 11.1 min 40% S-A.

Wavelength: λ=278 nm.

Flow rate: 1 mL/min

Injection: 10 μL.

Sample Preparation:

For whole or roughly crushed leaves: 50 g of leaves are crushed then sieved through a 0.355 μm sieve.

For leaf powders: Use 50 g of leaf powder as is.

Preparation of the Solutions

Control solutions:

Lawsone solution at 0.3 mg/mL in 1/1 methanol/ethanol. Dilute to 1/10, 1/20, 1/100 in 1/1 methanol/water.

Test solutions:

Test solution A (assay of the lawsone present in an extract)

Dissolve 50 mg of extract in 100 mL of 1/1 methanol/water. Dissolve with ultrasound. Filtration on Acrodisc GF GHP. Inject 10 μL.

Test solution B (assay of total lawsone)

Introduce 80 mg of leaf powder into a volumetric flask. Add 50 mL of 2N $H_2SO_4$. Heat to 97° C. for 30 min. Let cool. Add methanol qs 100 mL. Filter the solution on Acrodisc GF GHP 0.45 μm. Inject 10 μL of the filtrate.

Test solution C (assay of the lawsone formed by enzymes)

Introduce 80 mg of leaf powder into a volumetric flask. Add into 50 mL of demineralized water. Place in an ultrasound bath for 30 min between 30 and 40° C. Let cool. Add methanol qs 100 mL. Filter the solution on Acrodisc GF GHP 0.45 μm. Inject 10 μL of the filtrate.

Results

Use the regression line calculated with the control solutions to determine:

A. the lawsone content of the extract,

B. the total lawsone content, and/or

C. the content in lawsone formed by the enzymes.

Method 2: Assay of Nitrogen-Containing Compounds (Amino Acids, Proteins)

Free amino acids and proteins can be assayed before or after hydrolysis by ninhydrin spectrophotometry. The results are expressed in percentage of amino acids relative to asparagine.

Assay of Total Proteins and Amino Acids

Principle

Colorimetric assay of amino acids by the ninhydrin reagent after acid hydrolysis. The results are expressed in percentage of total amino acids relative to asparagine.

Reagents

Citrate buffer (pH=5)

Dissolve 2.1 g of citric acid in 20 mL of water, add 20 mL of 1 N sodium hydroxide and adjust to 50 mL with water.

Ninhydrin reagent:

Dissolve 0.08 g of tin (II) chloride ($SnCl_2$, $2H_2O$) in 50 ml of citrate buffer (pH=5).

Dissolve 2 g of ninhydrin in 50 mL ethylene glycol monomethyl ether (EGME).

Mix the two solutions.

6N hydrochloric acid

Dilute to ½ of concentrated hydrochloric acid (36%).

Diluent

Mix 100 mL of 1-propanol with 100 mL of water.

Preparation of the Solutions

Preparation of the calibration range

Dissolve 17 mg of asparagine in 100 mL of water.

Preparation of the test solutions

Weigh approximately 30 to 200 mg of extract depending on the sample to analyze ($pe_1$) in a screw thread tube, add 2 mL of 6N HCl.

Hermetically seal then place for around 16 hours at 110° C.

Neutralize with 3N sodium hydroxide (methyl red changes color) then adjust to 20 ml with water.

Assay

|  | T 0.1 | T 0.2 | T 0.5 | Test | Blank |
| --- | --- | --- | --- | --- | --- |
| Control solution (mL) | 0.1 | 0.2 | 0.5 | — | — |
| Test solution (mL) | — | — | — | 0.2 | — |
| Water (mL) | 1 | 1 | 1 | 1 | 1 |
| Ninhydrin reagent (mL) | 1 | 1 | 1 | 1 | 1 |

Stir and place in a water bath at 100° C. for 20 minutes.
Cool in an ice bath.
Adjust to 10 ml with diluent.
Measure the absorbance at 570 nm of the different solutions against the blank.
Calculations
Construct the calibration curve.
Deduce from it the total amino acid concentration ($Q_{AAT}$), expressed in asparagine, in the test solutions.
The total amino acid content ($T_{AAT}$) of the extract is given by the following formula:

$$T_{AAT}(\%) = \frac{Q_{AAT} \times 100 \times 20}{pe_1}$$

with: $Q_{AAT}$ in mg/ml
$pe_1$ in mg

Method 3: Weight Assay of Chlorophylls

The chlorophyll content in the extract may be evaluated by the weight obtained after washing the extract with heptane. The extract is taken up by 10 volumes of methanol. After stirring for 15 min, the solution is filtered. The supernatant is dried and constitutes the fraction containing chlorophylls.

Method 4: Spectrophotometric Assay of Phenol Compounds

The content of phenol compounds in the extract can be evaluated by spectrophotometry according to the method of the European Pharmacopoeia, version 9.0, 2.8.14.

The solutions to be tested are prepared by dissolving 25 mg of extract in 100 mL of water.

The content of phenol compounds is expressed by reference to pyrogallol.

Method 5: Colorimetric Assay of Saccharide Compounds Before and After Hydrolysis Principle: Colorimetric determination of saccharide compounds by dinitrosalicylic acid (DNS) compared to glucose before and after hydrolysis. The results are expressed as the percentage of saccharide compounds relative to glucose.

Reagents:
DNS reagents: dissolve 30 g of sodium and potassium ditartrate in 50 ml of water. Add 20 mL of 2N sodium hydroxide. Dissolve 1 g of dinitrosalicylic acid (DNS) while slightly heating. Make up to 100 mL with water.

Preparation of Solutions:
Preparation of the calibration range: dissolve 5 mg of glucose in 10 mL of water.
Preparation of hydrolyzed test solutions (total saccharide compounds): Weigh about 1 g of extract ($pe_2$). Add 1 mL of 4N H2SO4. Heat at reflux for 2 hours. Neutralize with 1N sodium hydroxide and transfer to a 20 mL volumetric flask. Make up to 20 mL with water.
Preparation of non-hydrolyzed test solutions (free saccharide compounds=monosaccharides): weight about 10 g of extract ($pe_3$) in a 20 mL volumetric flask. Make up to 20 mL with water.

Dosage: the solutions are dosed according to the following table:

|  | T 0.5 | T1 | T1.5 | T2 | Tests | Blank |
|---|---|---|---|---|---|---|
| Control solution (ml) | 0.5 | 1 | 1.5 | 2 | — | — |
| Test solution (ml) | — | — | — | — | 1 | — |
| Water (ml) | 1.5 | 1 | 0.5 | 0 | 1 | 2 |
| DNS | 1 | 1 | 1 | 1 | 1 | 1 |

Shake and then place for 5 minutes in a water bath at 100° C. Cool on an ice bath and make up to 10 mL with water. Measure the absorbance at 540 nm of the different solutions against the blank.

Calculation:
Construct the Calibration Curve.
Deduce the concentration of total saccharide compounds (QSRT) and free saccharides (QSRL), expressed as glucose, in the test solutions. The titer in total saccharide compounds (TSRT) of the extract is provided by the following formula:

$$T_{SRT}(\%) = \frac{Q_{SRT} \times 100 \times 20}{pe_2}$$

With $Q_{SRT}$ in mg/ml and $pe_2$ in mg
The titer in free saccharide compounds (TSRL) of the extract is provided by the following formula:

$$T_{SRL}(\%) = \frac{Q_{SRL} \times 100 \times 20}{pe_3}$$

With $Q_{SRL}$ in mg/ml and $pe_3$ in mg

The invention claimed is:

1. Process for preparing a lawsone-rich extract which comprises the steps of:
   a) macerating the aerial parts of *Lawsonia inermis* in water, at a pH ranging from 4 to 8 in order for the glycosylated lawsone derivatives initially present in the aerial parts of *Lawsonia inermis* to be partially or totally hydrolyzed enzymatically, to provide an aqueous solution containing lawsone;
   b) adding an organic solvent to the solution obtained in step a), said organic solvent being selected from $C_4$-$C_{12}$ linear, or branched, alcohols to provide an aqueous phase and an organic phase;
   c) collecting the organic phase obtained from step b); and
   d) concentrating the organic phase collected in step c) to obtain a lawsone-rich extract.

2. The process according to claim 1 wherein step (a) is conducted at a temperature ranging from 20° C. to 60° C.

3. The process according to claim 1 wherein step a) is conducted at a pH ranging from 5 to 7.5.

4. The process according to claim 1 wherein it does not include any step of changing the pH of the aqueous solution or the aqueous phase by addition of acid or base.

5. The process according to claim 1 wherein step a) is performed under stirring for 15 min to 2 h.

6. The process according to claim 1 wherein in step a) is performed in a volume of water whose weight is 2 to 15 times greater than the weight of the aerial parts of *Lawsonia inermis* subjected to maceration.

7. The process according to claim 1 wherein the organic solvent is a biosourced alcohol.

8. The process according to claim 1 wherein the organic solvent is $C_4$-$C_8$ linear or branched alcohols or any mixtures thereof.

9. The process according to claim 1 wherein the lawsone-rich extract obtained in step d) contains more than 50% of the lawsone initially present in the aerial parts of *Lawsonia inermis*, said lawsone being either in its free form or in the form of glycosylated derivatives in the aerial parts of *Lawsonia inermis* subjected to maceration.

10. The process according to claim 1 further comprising the step c') between step c) and d), the step c' comprising adding a carrier to the organic phase collected in step c) and a step e) of drying the extract after step d) to provide dry lawsone-rich extract.

11. The process according to claim 1, wherein the lawsone-rich extract obtained in step d) contains from 7 to 60% by weight of lawsone relative to the total weight of the dry extract and further comprises luteolin, apigenin and 2,3,4,6-tetrahydroxyacetophenone.

12. The process according to claim 1, wherein the lawsone-rich extract obtained in step d) further comprises coumaric acid and/or glycosylated luteolin.

13. The process according to claim 1 wherein the lawsone-rich extract obtained in step d) do not comprise more than 2% by weight of proteins, peptides or amino acids relative to the total weight of the dry extract.

14. The process according to claim 1 wherein the dry lawsone-rich extract obtained in step e) contains from 0.6 to 1.4% by weight of lawsone relative to the total weight of the dry extract and further comprises luteolin, apigenin and 2,3,4,6-tetrahydroxyacetophenone.

15. The process according to claim 14 wherein the dry lawsone-rich extract obtained in step e) further contains, relative to the total weight of the dry lawsone-rich extract:
  from 0.05 to 1.0% by weight of luteolin,
  from 0.01 to 0.5% by weight of apigenin, and
  from 0.05 to 1.0% by weight of 2,3,4,6-tetrahydroxyacetophenone.

16. The process according to claim 1 wherein the organic solvent is selected from the group consisting of n-butanol, sec-butanol, isobutanol and any mixtures thereof.

\* \* \* \* \*